US012642939B2

(12) United States Patent
Sepulveda et al.

(10) Patent No.: US 12,642,939 B2
(45) Date of Patent: Jun. 2, 2026

(54) CATHETER TIP STRUCTURE AND METHOD OF MANUFACTURE

(71) Applicant: Bard Access Systems, Inc., Salt Lake City, UT (US)

(72) Inventors: Juan Sepulveda, Centerville, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 749 days.

(21) Appl. No.: 17/969,626

(22) Filed: Oct. 19, 2022

(65) Prior Publication Data

US 2023/0126869 A1 Apr. 27, 2023

Related U.S. Application Data

(60) Provisional application No. 63/270,496, filed on Oct. 21, 2021.

(51) Int. Cl.
*B29C 43/02* (2006.01)
*A61M 25/00* (2006.01)
(Continued)

(52) U.S. Cl.
CPC .... *A61M 25/0068* (2013.01); *A61M 25/0009* (2013.01); *A61M 25/001* (2013.01);
(Continued)

(58) Field of Classification Search
CPC ........... A61M 25/0009; A61M 25/001; A61M 2025/0018; A61M 25/0026;
(Continued)

(56) References Cited

U.S. PATENT DOCUMENTS

| 1,013,691 A | 1/1912 | Shields |
| 1,906,678 A | 5/1933 | Wappler |

(Continued)

FOREIGN PATENT DOCUMENTS

| EP | 0730880 A1 | 9/1996 |
| EP | 2061385 A1 | 5/2009 |

(Continued)

OTHER PUBLICATIONS

EP 20862936.0 filed Mar. 28, 2022 Extended European Search Report dated Sep. 19, 2023.

(Continued)

*Primary Examiner* — Leo B Tentoni
(74) *Attorney, Agent, or Firm* — Rutan & Tucker LLP

(57) ABSTRACT

The distal tip structure of a rapidly insertable central catheter (RICC) can be required to perform different functions from that of the remaining, multi-luminal section, of the RICC catheter. As such, the catheter body can be formed of a first material and the distal tip structure can be formed of a second material. Forming the RICC requires joining these two materials while maintaining a smooth abluminal surface. A bifurcated plug including a second material can be placed within a first lumen or second lumen of the catheter body. A mandrel can be placed within a third lumen. The assembly can then be placed within a die to plastically deform the bifurcated plug into a distal tip structure. Advantageously, only a single structure is required to plug the lumen and form the distal tip structure, reducing complexity and associated costs.

10 Claims, 7 Drawing Sheets

(51) Int. Cl.

| | |
|---|---|
| *B29C 33/48* | (2006.01) |
| *B29C 43/18* | (2006.01) |
| *B29C 48/09* | (2019.01) |
| *B29C 65/48* | (2006.01) |

(52) U.S. Cl.

CPC ...... *A61M 25/003* (2013.01); *A61M 25/0043* (2013.01); *B29C 33/485* (2013.01); *A61M 2025/0018* (2013.01); *A61M 25/0026* (2013.01); *A61M 2025/0031* (2013.01)

(58) Field of Classification Search

CPC ........ A61M 25/003; A61M 2025/0031; A61M 25/0043; A61M 25/0068; B29C 33/485; B29C 43/02; B29C 43/18; B29C 48/09; B29C 65/48

USPC .... 264/150, 209.1, 259, 267, 313, 320, 325; 156/73.5, 244.13, 293

See application file for complete search history.

(56) References Cited

U.S. PATENT DOCUMENTS

| | | | |
|---|---|---|---|
| 3,225,762 | A | 12/1965 | Guttman |
| 3,710,781 | A | 1/1973 | Huthcins, IV et al. |
| 3,890,976 | A | 6/1975 | Bazell et al. |
| 4,205,675 | A | 6/1980 | Vaillancourt |
| 4,270,535 | A | 6/1981 | Bogue et al. |
| 4,292,970 | A | 10/1981 | Hession, Jr. |
| 4,468,224 | A | 8/1984 | Enzmann et al. |
| 4,525,157 | A | 6/1985 | Vaillancourt |
| 4,581,019 | A | 4/1986 | Curelaru et al. |
| 4,661,300 | A | 4/1987 | Daugherty |
| 5,004,455 | A | 4/1991 | Greenwood et al. |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,120,317 | A | 6/1992 | Luther |
| 5,135,599 | A | 8/1992 | Martin et al. |
| 5,167,623 | A | 12/1992 | Cianci et al. |
| 5,188,593 | A | 2/1993 | Martin |
| 5,195,962 | A | 3/1993 | Martin et al. |
| 5,207,650 | A | 5/1993 | Martin |
| 5,267,958 | A | 12/1993 | Buchbinder et al. |
| 5,295,970 | A | 3/1994 | Clinton et al. |
| 5,306,247 | A | 4/1994 | Pfenninger |
| 5,328,472 | A | 7/1994 | Steinke et al. |
| 5,350,358 | A | 9/1994 | Martin |
| 5,368,567 | A | 11/1994 | Lee |
| 5,378,230 | A | 1/1995 | Mahurkar |
| 5,380,290 | A | 1/1995 | Makower et al. |
| 5,389,087 | A | 2/1995 | Miraki |
| 5,439,449 | A | 8/1995 | Mapes et al. |
| 5,443,457 | A | 8/1995 | Ginn et al. |
| 5,489,271 | A | 2/1996 | Andersen |
| 5,573,520 | A | 11/1996 | Schwartz et al. |
| 5,645,528 | A | 7/1997 | Thome |
| 5,683,370 | A | 11/1997 | Luther et al. |
| 5,690,613 | A | 11/1997 | Verbeek |
| 5,718,678 | A | 2/1998 | Fleming, III |
| 5,772,636 | A | 6/1998 | Brimhall et al. |
| 5,810,789 | A | 9/1998 | Powers et al. |
| 5,885,251 | A | 3/1999 | Luther |
| 5,908,409 | A | 6/1999 | Rinehart et al. |
| 5,919,164 | A | 7/1999 | Andersen |
| 5,947,940 | A | 9/1999 | Beisel |
| 5,957,893 | A | 9/1999 | Luther et al. |
| 6,206,849 | B1 | 3/2001 | Martin et al. |
| 6,332,877 | B1 | 12/2001 | Michels |
| 6,475,187 | B1 | 11/2002 | Gerberding |
| 6,551,290 | B1 | 4/2003 | Elsberry et al. |
| 6,606,515 | B1 | 8/2003 | Windheuser et al. |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |
| 8,882,713 | B1 | 11/2014 | Call et al. |
| 8,900,192 | B2 | 12/2014 | Anderson et al. |
| 8,900,207 | B2 | 12/2014 | Uretsky |
| 8,915,884 | B2 | 12/2014 | Tal et al. |
| 8,956,327 | B2 | 2/2015 | Bierman et al. |
| 9,023,093 | B2 | 5/2015 | Pal |
| 9,138,252 | B2 | 9/2015 | Bierman et al. |
| 9,180,275 | B2 | 11/2015 | Helm |
| 9,265,920 | B2 | 2/2016 | Rundquist et al. |
| 9,272,121 | B2 | 3/2016 | Piccagli |
| 9,522,254 | B2 | 12/2016 | Belson |
| 9,554,785 | B2 | 1/2017 | Walters et al. |
| 9,566,087 | B2 | 2/2017 | Bierman et al. |
| 9,675,784 | B2 | 6/2017 | Belson |
| 9,713,695 | B2 | 7/2017 | Bunch et al. |
| 9,764,117 | B2 | 9/2017 | Bierman et al. |
| 9,770,573 | B2 | 9/2017 | Golden et al. |
| 9,814,861 | B2 | 11/2017 | Boutillette et al. |
| 9,820,845 | B2 | 11/2017 | von Lehe et al. |
| 9,861,383 | B2 | 1/2018 | Clark |
| 9,884,169 | B2 | 2/2018 | Bierman et al. |
| 9,889,275 | B2 | 2/2018 | Voss et al. |
| 9,913,585 | B2 | 3/2018 | McCaffrey et al. |
| 9,913,962 | B2 | 3/2018 | Tal et al. |
| 9,950,139 | B2 | 4/2018 | Blanchard et al. |
| 9,981,113 | B2 | 5/2018 | Bierman |
| 10,010,312 | B2 | 7/2018 | Tegels |
| 10,065,020 | B2 | 9/2018 | Gaur |
| 10,098,724 | B2 | 10/2018 | Adams et al. |
| 10,111,683 | B2 | 10/2018 | Tsamir et al. |
| 10,118,020 | B2 | 11/2018 | Avneri et al. |

(56) References Cited

U.S. PATENT DOCUMENTS

| | | |
|---|---|---|
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2001/0044594 A1 | 11/2001 | Martin et al. |
| 2002/0040231 A1 | 4/2002 | Wysoki |
| 2002/0107506 A1 | 8/2002 | McGuckin et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0193093 A1 | 9/2004 | Desmond |
| 2004/0230178 A1 | 11/2004 | Wu |
| 2005/0004554 A1 | 1/2005 | Osborne |
| 2005/0049552 A1 | 3/2005 | Holzapfel et al. |
| 2005/0245882 A1 | 11/2005 | Elkins et al. |
| 2005/0245887 A1 | 11/2005 | Olsen et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2008/0039796 A1 | 2/2008 | Nakajima |
| 2008/0045894 A1 | 2/2008 | Perchik et al. |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0093670 A1 | 4/2009 | Annest et al. |
| 2009/0221961 A1 | 9/2009 | Tal et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0209221 A1 | 8/2012 | Patterson et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0012924 A1 | 1/2013 | Davis et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094741 A1 | 4/2014 | Bellisario et al. |
| 2014/0100552 A1 | 4/2014 | Gallacher et al. |
| 2014/0155863 A1 | 6/2014 | Walker et al. |
| 2014/0180255 A1 | 6/2014 | LeBlanc et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Bamell |
| 2016/0114124 A1 | 4/2016 | Tal |
| 2016/0220786 A1 | 8/2016 | Mitchell et al. |
| 2016/0220795 A1 | 8/2016 | Korkuch et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035989 A1 | 2/2017 | Gilman |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0333681 A1 | 11/2017 | Di Caprio et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0193042 A1 | 7/2018 | Wilson et al. |
| 2018/0296799 A1 | 10/2018 | Horst et al. |
| 2018/0296804 A1 | 10/2018 | Bierman |
| 2018/0339131 A1 | 11/2018 | Muse et al. |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2020/0030124 A1 | 1/2020 | Bluecher et al. |
| 2020/0094025 A1 | 3/2020 | Wisman |
| 2021/0069471 A1 | 3/2021 | Howell |
| 2021/0121661 A1 | 4/2021 | Howell |
| 2021/0121667 A1 | 4/2021 | Howell |
| 2021/0187245 A1 | 6/2021 | Ishida |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0040447 A1 | 2/2022 | Mewissen |
| 2023/0132903 A1 | 5/2023 | Sepulveda et al. |
| 2023/0233796 A1 | 7/2023 | Howell |
| 2023/0233800 A1 | 7/2023 | Howell et al. |
| 2024/0091501 A1 | 3/2024 | Howell |

(56) References Cited

U.S. PATENT DOCUMENTS

| | | | |
|---|---|---|---|
| 2024/0181210 A1 | 6/2024 | Howell et al. | |
| 2024/0198042 A1 | 6/2024 | Sepulveda | |

FOREIGN PATENT DOCUMENTS

| | | | | |
|---|---|---|---|---|
| EP | 1458437 | B1 | 3/2010 | |
| EP | 2248549 | A2 | 11/2010 | |
| EP | 2319576 | A1 | 5/2011 | |
| EP | 2366422 | A1 | 9/2011 | |
| EP | 2486880 | A2 | 8/2012 | |
| EP | 2486881 | A2 | 8/2012 | |
| EP | 2486951 | A2 | 8/2012 | |
| EP | 2512576 | A2 | 10/2012 | |
| EP | 2152348 | B1 | 2/2015 | |
| EP | 3093038 | B1 | 5/2019 | |
| EP | 2260897 | B1 | 9/2019 | |
| ES | 2303546 | T3 | 8/2008 | |
| GB | 1273547 | A | 5/1972 | |
| WO | 94/21315 | A1 | 9/1994 | |
| WO | 95/32009 | A2 | 11/1995 | |
| WO | 98/44979 | A1 | 10/1998 | |
| WO | 98/53871 | A1 | 12/1998 | |
| WO | 99/12600 | A1 | 3/1999 | |
| WO | 99/26681 | A1 | 6/1999 | |
| WO | 2003008020 | A1 | 1/2003 | |
| WO | 2003057272 | A2 | 7/2003 | |
| WO | 2003066125 | A2 | 8/2003 | |
| WO | WO-2004037331 | A1 * | 5/2004 | .... A61M 2025/0031 |
| WO | 2006055288 | A2 | 5/2006 | |
| WO | 2006055780 | A2 | 5/2006 | |
| WO | 2007046850 | A2 | 4/2007 | |
| WO | 2008033983 | A1 | 3/2008 | |
| WO | 2008092029 | A2 | 7/2008 | |
| WO | 2008/131300 | A2 | 10/2008 | |
| WO | 2008131289 | A2 | 10/2008 | |
| WO | 2009114833 | A1 | 9/2009 | |
| WO | 2009114837 | A2 | 9/2009 | |
| WO | 2010/048449 | A2 | 4/2010 | |
| WO | 2010056906 | A2 | 5/2010 | |
| WO | 2010083467 | A2 | 7/2010 | |
| WO | 2010/132608 | A2 | 11/2010 | |
| WO | 2011081859 | A2 | 7/2011 | |
| WO | 2011097639 | A2 | 8/2011 | |
| WO | 2011146764 | A1 | 11/2011 | |
| WO | 2012068162 | A2 | 5/2012 | |
| WO | 2012068166 | A2 | 5/2012 | |
| WO | 2012135761 | A1 | 10/2012 | |
| WO | 2012162677 | A1 | 11/2012 | |
| WO | 2013026045 | A1 | 2/2013 | |
| WO | 2013138519 | A1 | 9/2013 | |
| WO | 2014006403 | A1 | 1/2014 | |
| WO | 2014/100392 | A1 | 6/2014 | |
| WO | 2014113257 | A2 | 7/2014 | |
| WO | 2014152005 | A2 | 9/2014 | |
| WO | 2014197614 | A2 | 12/2014 | |
| WO | 2015057766 | A1 | 4/2015 | |
| WO | 2016110824 | A1 | 7/2016 | |
| WO | 2016123278 | A1 | 8/2016 | |
| WO | 2016139590 | A1 | 9/2016 | |
| WO | 2016139597 | A2 | 9/2016 | |
| WO | 2016176065 | A1 | 11/2016 | |
| WO | 2018089275 | A1 | 5/2018 | |
| WO | 2018089285 | A1 | 5/2018 | |
| WO | 2018089385 | A1 | 5/2018 | |
| WO | 2018191547 | A1 | 10/2018 | |
| WO | 2018213148 | A1 | 11/2018 | |
| WO | 2018218236 | A1 | 11/2018 | |
| WO | 2019/146026 | A1 | 8/2019 | |
| WO | 2019199734 | A1 | 10/2019 | |
| WO | 2020069395 | A1 | 4/2020 | |
| WO | 2021050302 | A1 | 3/2021 | |
| WO | 2021/077103 | A1 | 4/2021 | |
| WO | 2021062023 | A1 | 4/2021 | |
| WO | 2021081205 | A1 | 4/2021 | |
| WO | 2021086793 | A1 | 5/2021 | |
| WO | 2023069553 | A2 | 4/2023 | |
| WO | 2023081314 | A1 | 5/2023 | |
| WO | 2023141112 | A1 | 7/2023 | |
| WO | 2023146773 | A3 | 9/2023 | |
| WO | 2024123925 | A2 | 6/2024 | |
| WO | 2024129815 | A1 | 6/2024 | |

OTHER PUBLICATIONS

PCT/US2023/010971 filed Jan. 17, 2023 International Search Report and Written Opinion dated Jul. 28, 2023.

U.S. Appl. No. 17/006,553, filed Aug. 28, 2020 Non-Final Office Action dated Jun. 26, 2023.

U.S. Appl. No. 17/006,553, filed Aug. 28, 2020 Notice of Allowance dated Sep. 11, 2023.

Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, No. 4, Feb. 5, 2008 [Feb. 5, 2008] pp. 847-853.

PCT/US2020/048583 filed Aug. 28, 2020 International Search Report and Written Opinion dated Nov. 13, 2020.

PCT/US2020/052536 filed Sep. 24, 2020 International Search Report and Written Opinion dated Dec. 4, 2020.

PCT/US2020/056364 filed Oct. 19, 2020 International Search Report and Written Opinion dated Jan. 19, 2021.

PCT/US2020/056864 filed Oct. 22, 2020 International Search Report and Written Opinion dated Jan. 14, 2021.

PCT/US2020/057202 filed Oct. 23, 2020 International Search Report and Written Opinion dated Jan. 21, 2021.

PCT/US2020/057397 filed Oct. 26, 2020 International Search Report and Written Opinion dated Mar. 10, 2021.

PCT/US2021/014700 filed Jan. 22, 2021 International Search Report and Written Opinion dated Jun. 29, 2021.

PCT/US2021/028018 filed Apr. 19, 2021 International Search Report and Written Opinion dated Sep. 13, 2021.

PCT/US2021/028683 filed Apr. 22, 2021 International Search Report and Written Opinion dated Sep. 16, 2021.

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2021/039084 filed Jun. 25, 2021 International Search Report and Written Opinion dated Jan. 10, 2022.

PCT/US2021/039843 filed Jun. 30, 2021 International Search Report and Written Opinion dated Nov. 11, 2021.

PCT/US2021/044029 filed Jul. 30, 2021 International Search Report and Written Opinion dated Dec. 9, 2021.

U.S. Appl. No. 15/008,628, filed Jan. 28, 2016 Final Office Action dated May 30, 2018.

U.S. Appl. No. 15/008,628, filed Jan. 28, 2016 Non-Final Office Action dated Jan. 25, 2019.

U.S. Appl. No. 15/008,628, filed Jan. 28, 2016 Non-Final Office Action dated Nov. 2, 2017.

U.S. Appl. No. 15/008,628, filed Jan. 28, 2016 Notice of Allowance dated May 15, 2019.

U.S. Appl. No. 16/398,020, filed Apr. 29, 2019 Final Office Action dated Jan. 25, 2022.

U.S. Appl. No. 16/398,020, filed Apr. 29, 2019 Non-Final Office Action dated May 11, 2021.

U.S. Appl. No. 17/006,553, filed Aug. 28, 2020 Final Office Action dated Sep. 28, 2022.

U.S. Appl. No. 17/006,553, filed Aug. 28, 2020 Non-Final Office Action dated Mar. 16, 2022.

U.S. Appl. No. 17/077,728, filed Oct. 22, 2020 Non-Final Office Action dated Feb. 9, 2022.

PCT/US2022/047179 filed Oct. 19, 2022 International Search Report and Written Opinion dated Apr. 18, 2023.

PCT/US2022/048881 filed Nov. 3, 2022 International Search Report and Written Opinion dated Mar. 31, 2023.

PCT/US2023/010972 filed Jan. 17, 2023 International Search Report and Written Opinion dated May 30, 2023.

(56)     References Cited

OTHER PUBLICATIONS

PCT/US2023/082753 filed Dec. 6, 2023 International Search Report and Written Opinion dated May 29, 2024.

U.S. Appl. No. 17/363,500, filed Jun. 30, 2021 Non-Final Office Action dated Sep. 23, 2024.

PCT/US2022/047179 filed Oct. 19, 2022 International Preliminary Report on Patentability dated Apr. 23, 2024.

PCT/US2023/083764 filed Dec. 13, 2023 International Search Report and Written Opinion dated Apr. 22, 2024.

U.S. Appl. No. 17/363,500, filed Jun. 30, 2021 Restriction Requirement dated Jul. 16, 2024.

U.S. Appl. No. 17/363,500, filed Jun. 30, 2021 Final Office Action dated Feb. 20, 2025.

U.S. Appl. No. 17/363,500, filed Jun. 30, 2021 Non-Final Office Action dated Sep. 4, 2025.

U.S. Appl. No. 17/980,455, filed Nov. 3, 2022 Restriction Requirement dated Nov. 19, 2025.

U.S. Appl. No. 18/076,169, filed Dec. 6, 2022 Non-Final Office Action dated Aug. 8, 2025.

U.S. Appl. No. 18/076,169, filed Dec. 6, 2022 Notice of Allowance dated Dec. 5, 2025.

U.S. Appl. No. 18/081,480, filed Dec. 14, 2022 Non-Final Office Action dated Sep. 17, 2025.

U.S. Appl. No. 18/098,052, filed Jan. 17, 2023 Restriction Requirement dated Dec. 5, 2025.

U.S. Appl. No. 18/098,059, filed Jan. 17, 2023 Restriction Requirement dated Nov. 20, 2025.

U.S. Appl. No. 17/363,500, filed Jun. 30, 2021 Notice of Allowance dated Jan. 27, 2026.

U.S. Appl. No. 18/081,480, filed Dec. 14, 2022 Final Office Action dated Mar. 30, 2026.

U.S. Appl. No. 18/098,052, filed Jan. 17, 2023 Non-Final Office Action dated Feb. 23, 2026.

U.S. Appl. No. 18/098,059, filed Jan. 17, 2023 Ex Parte Quayle Action dated Mar. 26, 2026.

U.S. Appl. No. 18/524,480, filed Nov. 30, 2023 Non-Final Office Action dated Mar. 25, 2026.

* cited by examiner

PROXIMAL

130

162

150

160

156

140

152

158

154

130

122

120

DISTAL

TRANSVERSE

LATERAL

LONGITUDINAL

100

PROXIMAL

DISTAL

PROXIMAL

DISTAL

SECTION A

SECTION B

SECTION C

SECTION D OR E

PROXIMAL

DISTAL

DISTAL             PROXIMAL

150

DISTAL PROXIMAL

CATHETER TIP STRUCTURE AND METHOD OF MANUFACTURE

PRIORITY

This application claims the benefit of priority to U.S. Provisional Application No. 63/270,496, filed Oct. 21, 2021, which is incorporated by reference in its entirety into this application.

SUMMARY

Briefly summarized, embodiments disclosed herein are directed to distal tip structures for a catheter, such as a rapidly insertable central catheter (RICC), and associated methods of manufacture. RICC systems include a catheter having a multi-luminal section defining two or more lumen, an access section defining a single lumen, and a dilator section disposed therebetween. The configuration of the RICC catheter allows a clinician to access the vasculature, dilate the access site, and place the multi-luminal section in a single step, mitigating the introduction and removal of multiple tools to achieve each of these steps separately. Forming the RICC catheter requires coupling the three different structures of the multi-luminal section, dilator section, and access section together, while maintaining a smooth outer profile. Each of the three different structures are required to display different mechanical properties to fulfil the respective roles in the placement process. Disclosed herein is a method of manufacture of a distal tip structure of a RICC catheter.

Disclosed herein is a method of forming a catheter including, extruding a multi-luminal section of a catheter body having a first catheter lumen and a second catheter lumen, forming a distal tip structure of the catheter body including, placing a first tine of a bifurcated plug within the first catheter lumen, placing a second tine of the bifurcated plug within the second catheter lumen, a distal tip of the bifurcated plug extending distally of a distal end of the catheter body, and forming the bifurcated plug into the distal tip structure, coupled to the multi-luminal section.

In some embodiments, the multi-luminal section is formed of a first material and the bifurcated plug is formed of a second material, different from the first material. In some embodiments, the first material includes a more compliant, or softer durometer, mechanical properties relative to the second material. In some embodiments, the distal tip structure includes one or both of a dilator section and an access section. In some embodiments, the step of forming the bifurcated plug into the distal tip structure further includes placing a portion of the bifurcated plug and a distal end of the multi-luminal section into a die and applying one or more of pressure, thermal energy, radio frequency energy, or ultrasonic energy to plastically deform the bifurcated plug into the distal tip structure. In some embodiments the method further includes, placing a mandrel within a third lumen of the multi-luminal section to define a portion of a distal lumen within the distal tip structure. In some embodiments, the bifurcated plug includes one of a rod or a tube folded in half and wherein a first end defines the first tine, and the second end defines the second tine.

Also disclosed is a method of forming a distal tip structure for a catheter including, forming a catheter body including a multi-luminal section having a first material and defining a first lumen and a second lumen, placing a proximal end of a mandrel within a distal end of the first lumen, placing a portion of the mandrel, a distal end of the multi-luminal section, and a pellet of a second material, different from the first material, within a die, and plastically deforming the pellet around the portion of the mandrel to form the distal tip structure coupled to the distal end of the multi-luminal section.

In some embodiments, the first material is relatively more compliant, elastically deformable, or a softer durometer relative to the second material. In some embodiments, the distal tip structure includes a dilator section and a portion of an access section. In some embodiments, the distal tip structure includes a dilator section having a recess configured to receive a proximal portion of an access section therein. In some embodiments, the method further includes coupling the proximal portion of the access section with the recess using adhesive, bonding, or welding.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
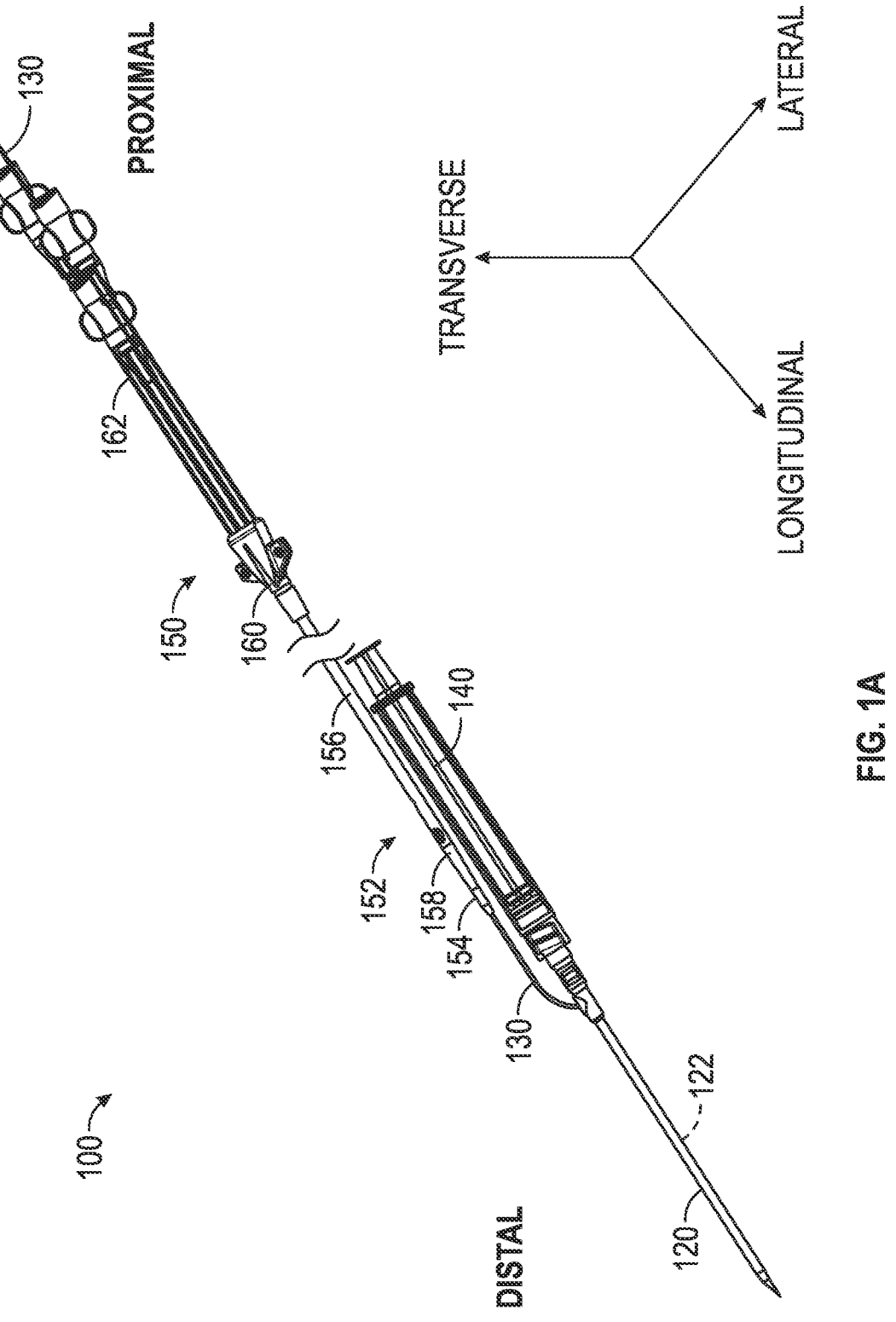
FIG. 1A shows a perspective view of a RICC system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figures 1B, 2:
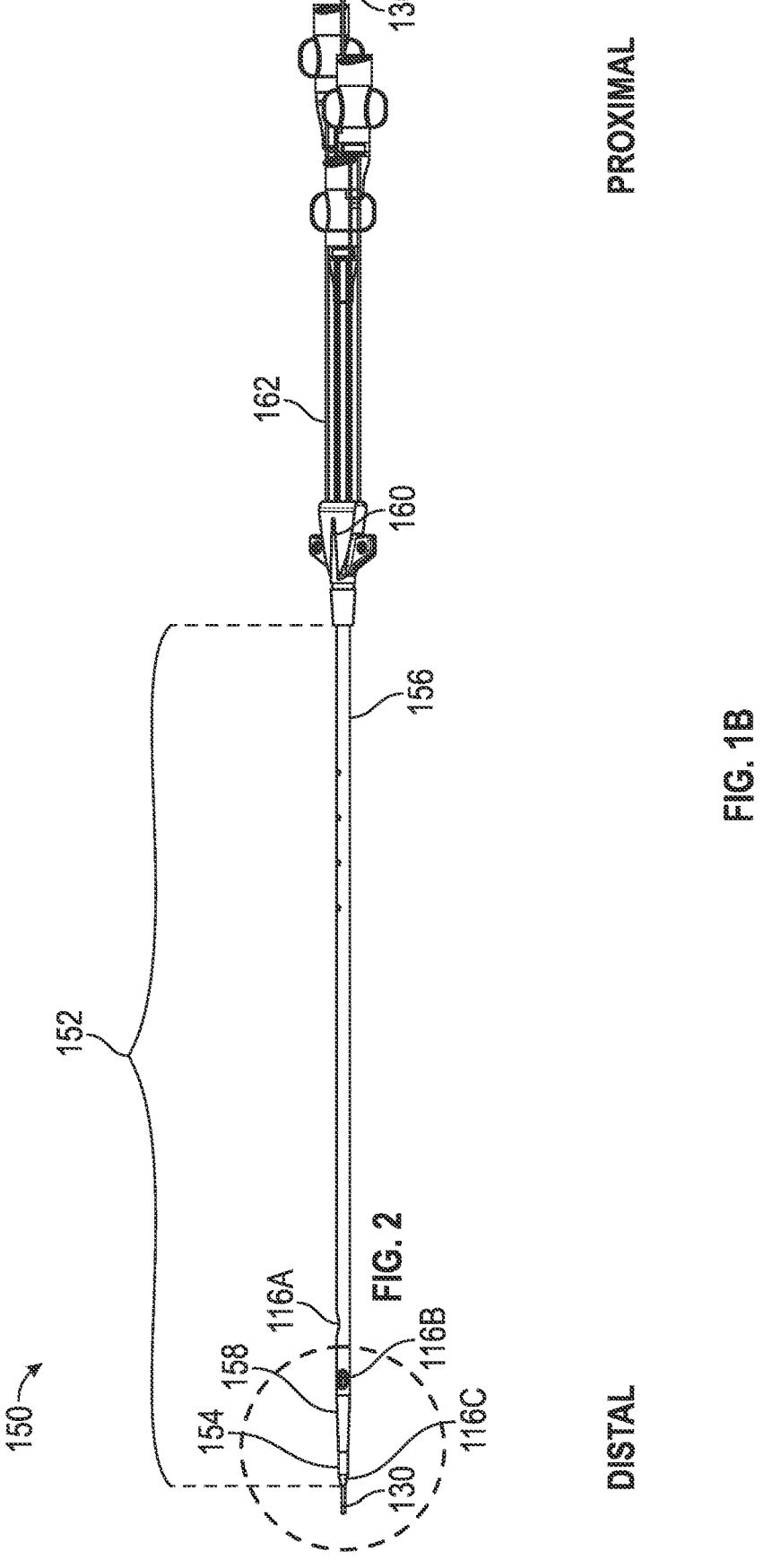
FIG. 1B shows a side view of a catheter of the RICC system of FIG. 1A, in accordance with embodiments disclosed herein.
FIG. 2 shows close up detail of a distal portion of the catheter of FIG. 1B, in accordance with embodiments disclosed herein.
Figure 2:
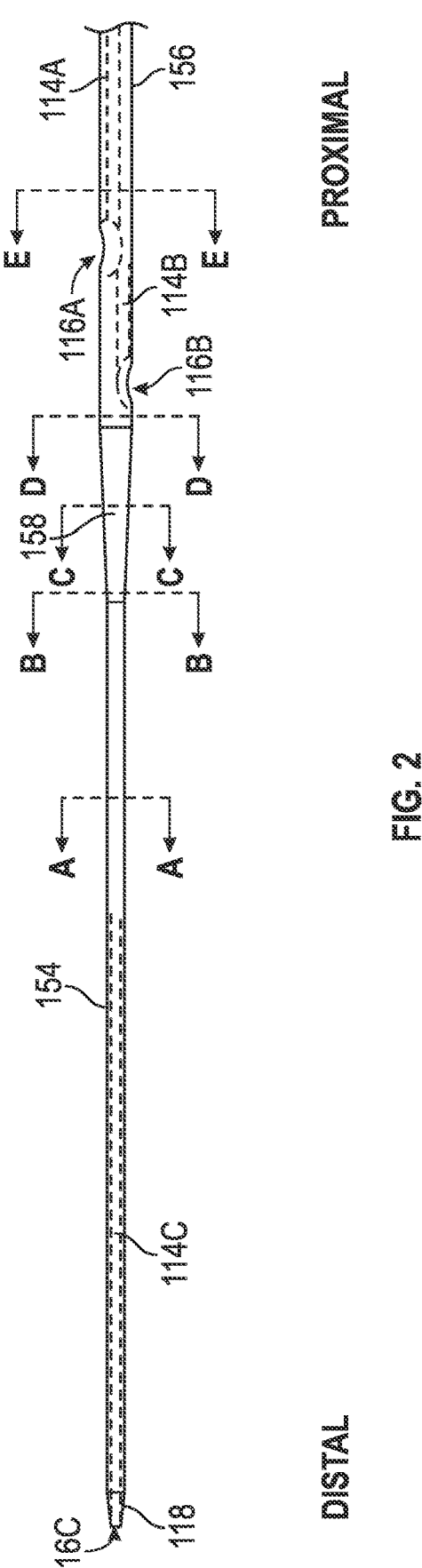

FIGS. 1A-1B show details of an exemplary Rapidly Insertable Central Catheter (RICC) placement system ("placement system") 100 generally including a needle 120, a guidewire 130, a syringe system 140, and a RICC catheter 150. The RICC catheter 150 can generally include a catheter body 152 supported at a proximal end by a catheter hub ("hub") 160. The hub 160 can include one or more extension legs 162 extending proximally therefrom. Each extension leg of the one or more extension legs 162 can be in fluid communication with a lumen of the catheter body 152. The catheter body 152 can include an access section 154, a multi-luminal section 156, and a dilator section 158 disposed therebetween. A guidewire 130 can extend through a lumen of the RICC catheter 150 from a proximal end of an extension leg 162, to a distal tip of the access section 154.

In an exemplary method of placing the RICC catheter 150, the needle 120 can be urged distally into the patient and access a vasculature, forming an insertion site. A syringe system 140, or similar device can draw a fluid flow proximally through a needle lumen 122 to observe a color and/or pulsatile flow and confirm correct vascular access. Once correct vascular access has been confirmed, the guidewire 130 can then be advanced through the needle lumen 122 and into the vasculature to maintain patency of the insertion site. The needle 120 and syringe system 140 assembly can then be withdrawn proximally. In an embodiment, a distal tip of the guidewire 130 can reside within the needle lumen 122 during venipuncture, which can expedite accessing the vasculature once venous access is confirmed and can maintain patency of the insertion site.

The RICC 150 can then be advanced over the guidewire 130 and into the vasculature. The access section 154 of the RICC 150, having only a single lumen, defines a relatively small outer diameter and can enter the vasculature over the guidewire 130, anchoring the insertion site. The dilator section 158 can then dilate the insertion site to allow the relatively larger diameter, multi-luminal section 156 which defines two or more lumen, to enter the vasculature. Once the RICC 150 has been placed, the guidewire 130 can be withdrawn proximally. Further details and embodiments of RICC systems 100 can be found, for example, in U.S. Pat. No. 10,376,675, U.S. 2019/0255294, U.S. 2021/0069471, U.S. 2021/0085927, U.S. 2021/0113809, U.S. 2021/0113810, U.S. 2021/0121661, U.S. 2021/0228843, U.S. 2021/0283368, U.S. 2021/0283381, U.S. 2021/0322729, U.S. 2021/0330941, U.S. 2021/0330942, U.S. 2021/0361915, U.S. 2021/0379336, U.S. 2021/0402142, U.S. 2021/0402149, U.S. 2021/0402153, U.S. 2021/0121667, U.S. 2022/0001138, U.S. 2022/0032013, U.S. 2022/0032014, U.S. 2022/0062528, U.S. 2022/0126064, U.S. 2022/0152368, U.S. 2022/0176081, U.S. 2022/0176082, U.S. 2022/0193376, U.S. 2022/0193377, U.S. 2022/0193378, U.S. 2022/0193379, and U.S. 2022/0296862, each of which is incorporated by reference in its entirety into this application.

As set forth herein, different portions of the RICC catheter 150 are required to perform different functions and as such are required to display different mechanical properties. For example, the access section 154 and/or the dilator section 158 can include more rigid mechanical properties, or a harder durometer material, relative to the multi-luminal section 156. As such, the access section 154 and dilator section 158 can withstand greater axial forces without kinking or collapsing, as theses sections are urged distally forming and dilating the insertion site. The multi-luminal section 156 can be formed of a relatively softer durometer, or a more compliant material, to facilitate negotiating through tortuous vascular pathways. Forming the RICC catheter 150 requires the coupling together of these different structures, formed of different materials, while maintaining a smooth abluminal surface.

FIG. 2 shows further details of a distal portion of the RICC catheter 150, including the access section 154, the dilator section 158, and a distal portion of the multi-luminal section 156. In an embodiment, the multi-luminal section 156 can include a proximal lumen 114A terminating at a proximal lumen aperture 116A, and a medial lumen 114B terminating at a medial lumen aperture 116B. Each of the proximal lumen aperture 116A and the medial lumen aperture 116B can extend through a side wall of the multi-luminal section 156. Each of the proximal lumen aperture 116A and the medial lumen aperture 116B can be disposed proximally of the dilator section 158. In an embodiment, the proximal lumen aperture 116A can be disposed proximally of the medial lumen aperture 116B. In an embodiment, the proximal lumen aperture 116A and the medial lumen aperture 116B can be disposed equidistant from the catheter hub 160.

Figure 3:
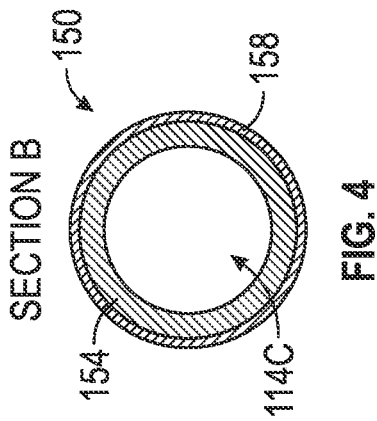
FIGS. 3-6 show various cross-sectional views of the distal portion of FIG. 2, in accordance with embodiments disclosed herein.

FIG. 3 shows a cross section view of the access section 154 at point "A" of FIG. 2. As shown, the access section 154 can define a single lumen and a relatively smaller outer diameter. A distal lumen 114C of the RICC catheter 150 can extend to a distal tip 118 of the RICC catheter 150 and can communicate with a distal lumen aperture 116C.

Figure 4:
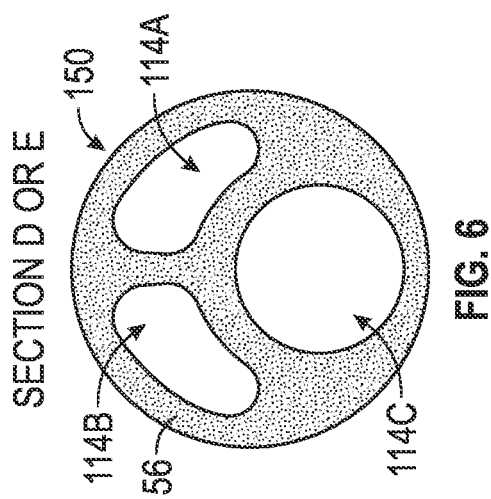

FIG. 4 shows a cross section view of the junction between the access section 154 and the dilator section 158, at point "B" of FIG. 2, where a portion of the access section 154 is received within the dilator section 158.

Figure 5:
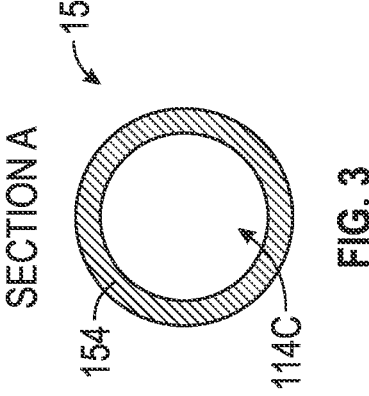

FIG. 5 shows a cross section view of the dilator section 158 at point "C" of FIG. 2, where an axis of the distal lumen 114C is offset from an axis of the dilator section 158 as the distal lumen 114 transitions between the multi-luminal section 156 and the access section 154.

Figure 6:
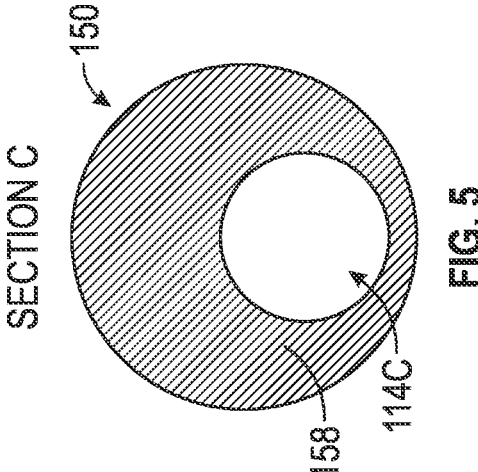

FIG. 6 shows a cross section view of the multi-luminal section 156 at points "D" or "E" of FIG. 2, showing the proximal lumen 114A, the medial lumen 114B and the distal lumen 114C.

Tip Forming Methods

Figures 6, 7:
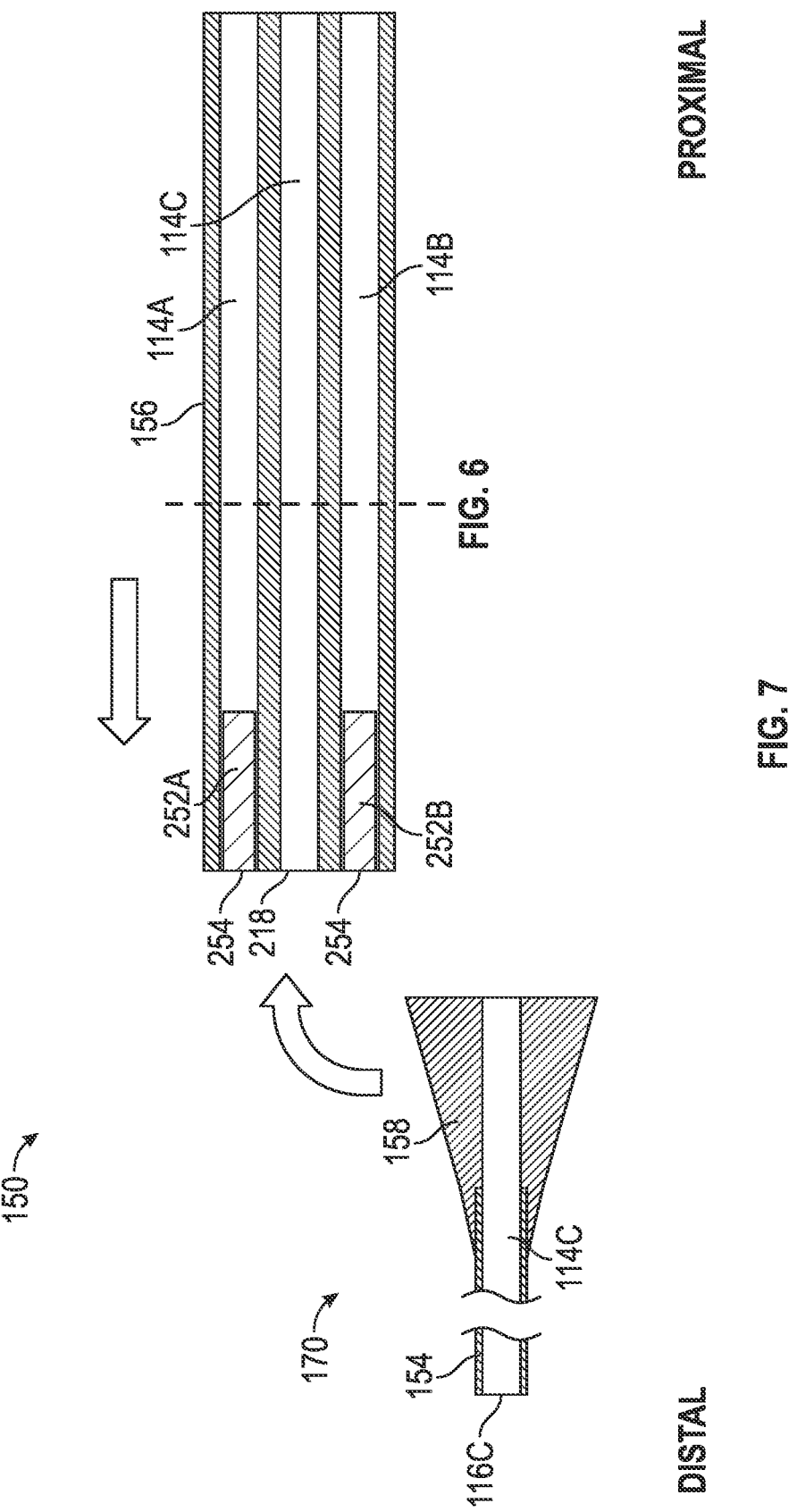
FIG. 7 shows an exemplary method of forming a distal tip structure of a catheter body, in accordance with embodiments disclosed herein.

FIG. 7 shows an exemplary method of manufacturing a catheter 150 including a distal tip structure 170 having one or both of the access section 154 and the dilator section 158. In an exemplary method of coupling a distal tip structure 170 to a multi-luminal section 156 to form a catheter body 152, termed "tipping," the multi-luminal section 156 can be formed having one or more lumen 114. In an embodiment, the multi-luminal section 156 can be extruded and trimmed to a desired length. It will be appreciated, however, that other methods of forming a multi-luminal section 156 are also contemplated. As shown in FIG. 7, a triple lumen multi-luminal section 156 is provided including a first (proximal) lumen 114A, a second (medial) lumen 114B, and a third (distal) lumen 114C. However, it will be appreciated that other single or multi-lumen catheters 150 are also contemplated. To note, the lumen 114A, 114B, 114C of the multi-luminal section 156 can be arranged radially about a central axis of the multi-luminal section 156, as shown in FIG. 6. In FIG. 7, the lumens 114A, 114B, 114C are shown adjacent to each other for clarity. It will be appreciated, however, that other configurations of multi-lumen catheters 150 are also contemplated.

In an embodiment, a plug 252 can be disposed into one or more lumen 114. For example, a first plug 252A can be disposed within a distal end of a first lumen 114A, and a second plug 252B can be disposed within a distal end of a second lumen 114B. A distal tip 254 of the plug 252 can align with a distal end 218 of the multi-luminal section 156. Optionally, a distal tip 254 of the plug 252 can be trimmed to align with a distal end 218 of the multi-luminal section 156.

The distal tip structure 170 can then be coupled with a distal end 218 of the multi-luminal section 156 using adhesive, bonding, solvent bonding, welding or the like. A lumen of the distal tip structure 170 can align with a lumen of the multi-luminal section 156 to form a distal lumen 114C extending to a distal lumen aperture 116C. The first plug 252A can seal a distal end of the proximal lumen 114A, and the second plug 252B can seal a distal end of the medial lumen 114B, proximally of the dilator section 158. The proximal lumen aperture 116A can then be formed through a wall of the multi-luminal section 156 and communicate with the proximal lumen 114A. The medial lumen aperture 116B can then be formed through a wall of the multi-luminal section 156 and communicate with the medial lumen 116B.

Figure 8A:
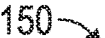
FIGS. 8A-8C show an exemplary method of forming a distal tip structure of a catheter body, in accordance with embodiments disclosed herein.
Figure 8A:
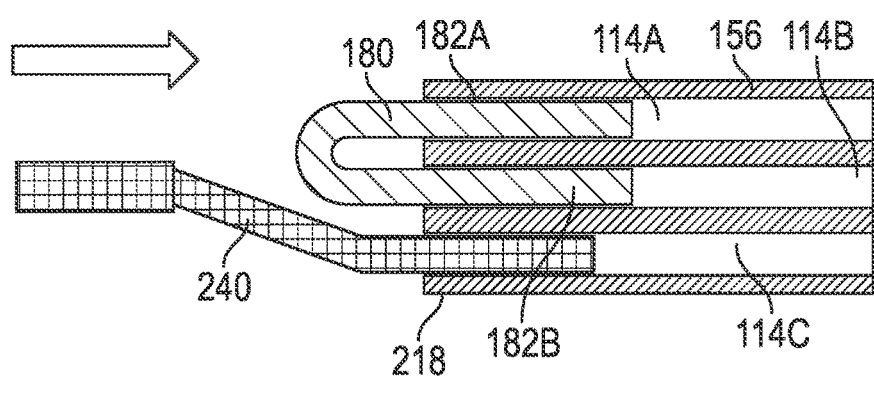
Figure 8B:
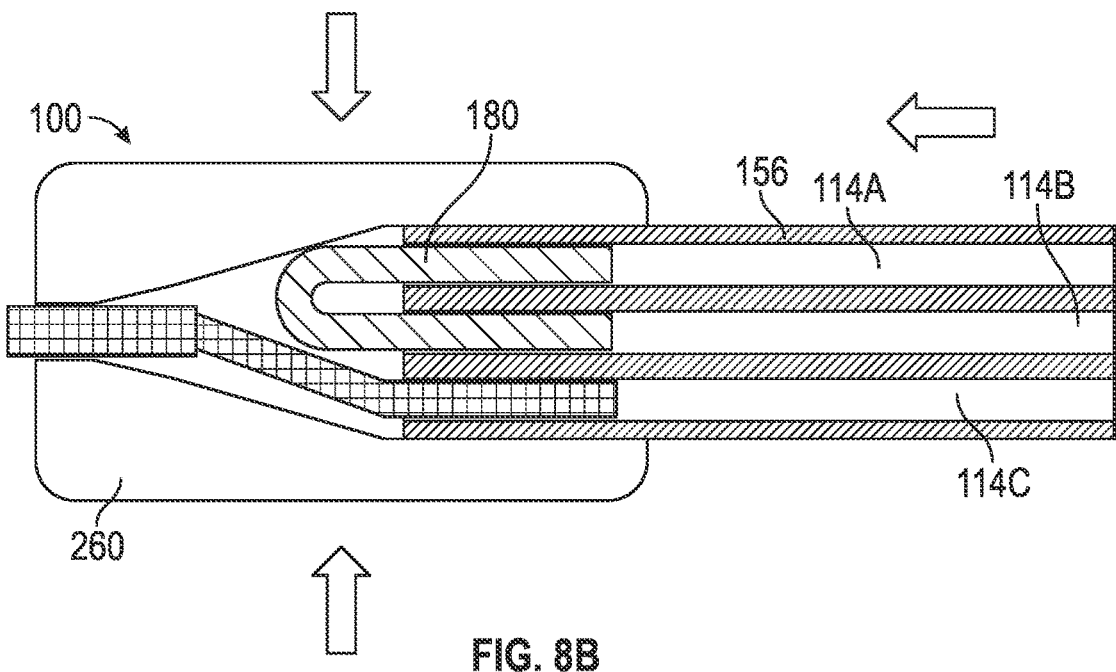
Figure 8C:
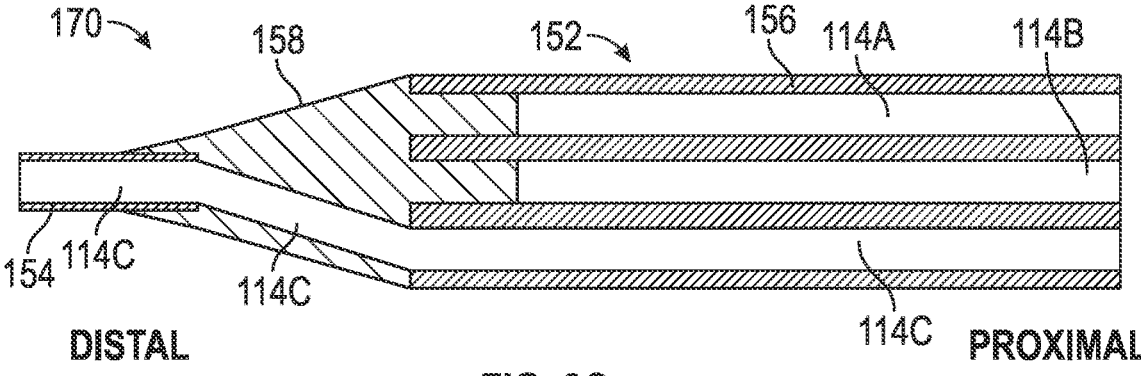

FIGS. 8A-8C show an exemplary method of forming a catheter 150 having a distal tip structure 170 including one or more of a dilator section 158 and an access section 154. As shown in FIG. 8A, a multi-luminal section 156 of the catheter body 152 is formed including one or more lumen 114, as described herein. In an embodiment, the multi-luminal section 156 can be formed of a first material.

In an embodiment, a bifurcated plug 180 can be provided including a second material different from the first material, and including one or more tines 182. As shown in FIG. 8A, the bifurcated plug 180 can include a first tine 182A and a second tine 182B. The first tine 182A can be disposed within a first lumen 114A, and the second tine 182B can be disposed within a second lumen 114B. In an embodiment, the bifurcated plug 180 can include a polymeric rod or a polymeric tube folded in half with a first end defining the first tine 182A and a second end defining the second tine 182B. To note, a distal end of the bifurcated plug 180 can extend distally of a distal end 218 of the multi-luminal section 156. In an embodiment, a proximal end of a mandrel 240 can be placed in the third lumen 114C and can define a pathway for a portion of the distal lumen 114C as it extends from the multi-luminal section 156 to the access section 154.

As shown in FIG. 8B, the distal end 218 of the multi-luminal section 156, including one or both of the bifurcated plug 180 and the mandrel 240, can then be placed within a die 260. Energy (thermal energy, radio frequency (RF) energy, ultrasonic, or the like) and/or pressure can be applied to the distal end 218 of the multi-luminal section 156 and the bifurcated plug 180 assembly to plastically deform the bifurcated plug 180 into at least a portion of the distal tip structure 170. The mandrel 240 can define a portion of the distal lumen 114C extending therethrough. In an embodiment, the distal tip structure 170 can define one or both of the dilator section 158 and the access section 154. In an embodiment, the distal tip structure 170 can include the dilator section 158 and can define a recess configured to receive a proximal end of the access section 154. Optionally, the access section 154 can be formed of a third material, different from both the first material and the second material and displaying different mechanical properties, durometers, or the like. The proximal end of the access section 154 can then be coupled with the dilator section 158 using adhesive, bonding, welding, or the like.

Advantageously, the material of the bifurcated plug 180 used to occlude the proximal lumen 114A and the medial lumen 114B, can be used to form the dilator section 158. As such, only a single structure is required to both occlude the lumen and form the distal tip structure 170, rather than two or more separate structures. This simplifies the manufacturing process and reduces associated costs.

Figure 9A:
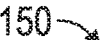
FIGS. 9A-9C show an exemplary method of forming a distal tip structure of a catheter body, in accordance with embodiments disclosed herein.
Figure 9A:
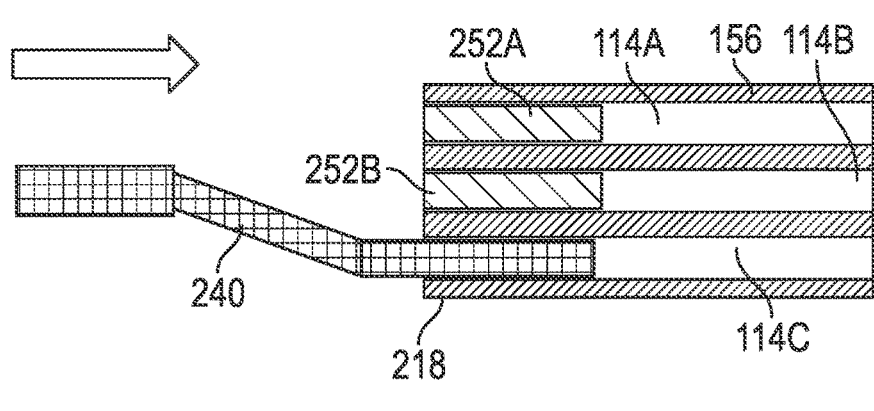
Figure 9B:
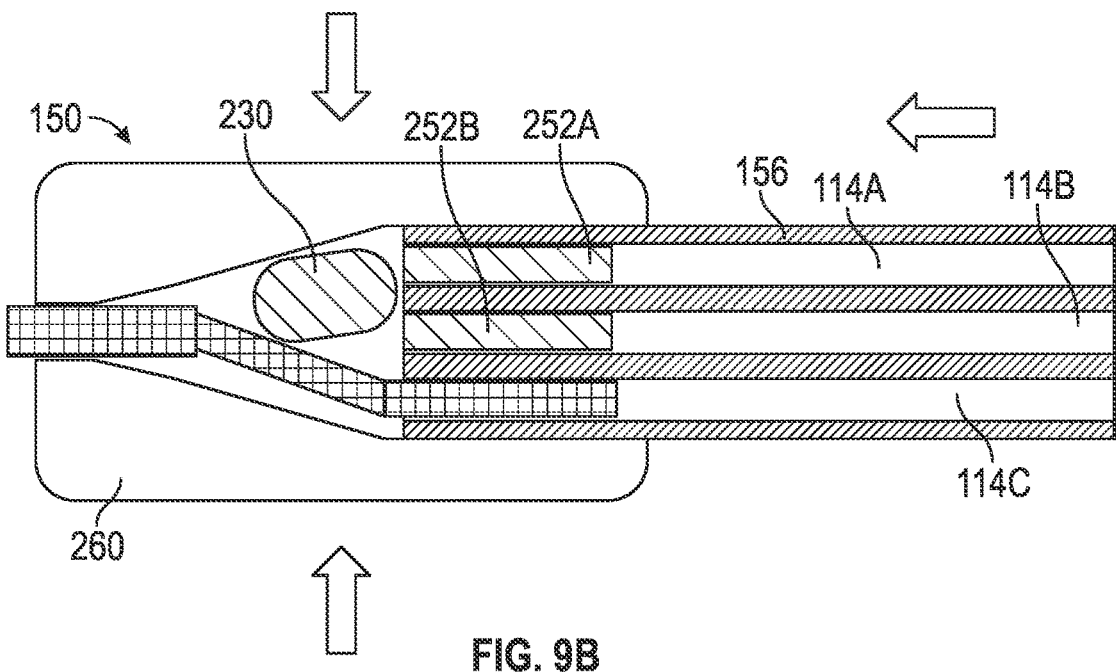
Figure 9C:
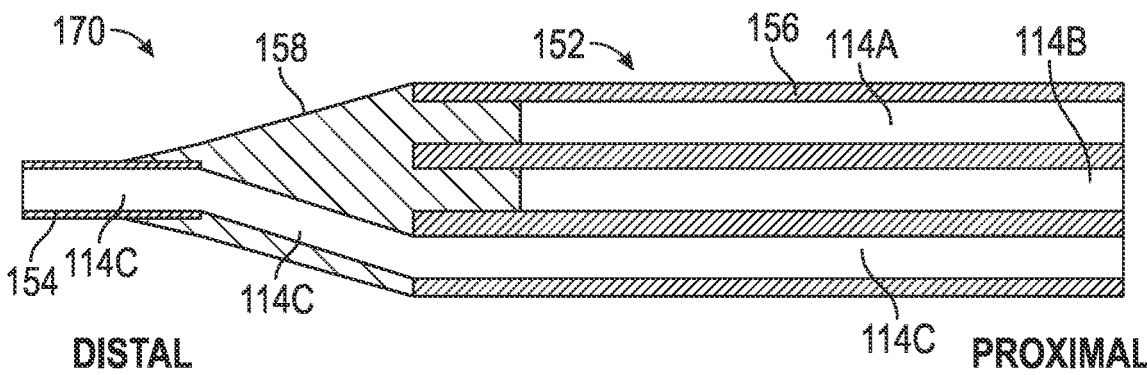

In an embodiment, as shown in FIGS. 9A-9C, the multi-luminal section 156 and mandrel 240 assembly can be provided, as described herein. The multi-luminal section 156 can be formed of a first material. The multi-luminal section 156 can include one or more plugs 252. The multi-luminal section 156, plug(s) 252, and mandrel 240 assembly can then be placed within the die 260 along with a pellet 230 of polymeric material formed of a second material within the die 260. Energy (thermal, RF, ultrasonic, or the like) and/or pressure can be applied to the distal end 218, mandrel 240, and pellet 230 assembly to plastically deform the pellet 230 into the distal tip structure 170.

In an embodiment, the multi-luminal section 156 can be formed of a first material and the plug 252 and/or pellet 230 can be formed of a second material, different from the first material. In an embodiment, the second material can display different mechanical properties from the first material. In an embodiment, one of the first material, second material, or third material can be a plastic, polymer, polyurethane, composite, elastomer, or the like. In an embodiment, the second material can display more rigid, or harder durometer, mechanical properties relative to the first material that can display more compliant or softer durometer mechanical properties. In an embodiment, the third material can display more or less rigid, or greater or lesser durometer, relative to one or both of the first material and the second material.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of forming a catheter, comprising:
   extruding a multi-luminal section of a catheter body formed of a first material and having a first catheter lumen, a second catheter lumen, and a third catheter lumen; and
   forming a distal tip structure coupled to the multi-luminal section of the catheter body, comprising:
   placing a proximal end of a mandrel within a distal end of the third catheter lumen;
   placing a portion of the mandrel, a distal end of the multi-luminal section of the catheter body, and a pellet of a second material, different from the first material, within a die; and
   deforming the pellet around the mandrel to form the distal tip structure of the catheter, thereby occluding the first catheter lumen and the second catheter lumen at the distal end of the catheter body and extending the third catheter lumen from the distal end of the catheter body through the distal tip structure of the catheter.

2. The method according to claim 1, wherein the first material is more compliant, or of a softer durometer, relative to the second material.

3. The method according to claim 1, wherein the distal tip structure of the catheter includes a dilator section, an access section, or both.

4. The method according to claim 1, wherein deforming the pellet around the mandrel to form the distal tip structure of the catheter further includes applying one or more of pressure, thermal energy, radio frequency energy, or ultrasonic energy to plastically deform the pellet into the distal tip structure of the catheter.

5. The method according to claim 1, wherein placing the proximal end of the mandrel within the third catheter lumen of the multi-luminal section of the catheter body and deforming the pellet around the mandrel defines the third catheter lumen within the distal tip structure when forming the distal tip structure of the catheter.

6. A method of forming a distal tip structure for a catheter, comprising:
   forming from a first material a catheter body including a multi-luminal section defining a first lumen and a second lumen;
   placing a proximal end of a mandrel within a distal end of the first lumen;
   placing a portion of the mandrel, a distal end of the multi-luminal section of the catheter body, and a pellet of a second material, different from the first material, within a die; and
   plastically deforming the pellet around the portion of the mandrel to form the distal tip structure of the catheter coupled to the distal end of the multi-luminal section of the catheter body, thereby occluding the second lumen at the distal end of the catheter body and extending the first lumen from the distal end of the catheter body through the distal tip structure of the catheter.

7. The method according to claim 6, wherein the first material is relatively more compliant, elastically deformable, or of a softer durometer relative to the second material.

8. The method according to claim 6, wherein the distal tip structure of the catheter includes a dilator section and a portion of an access section.

9. The method according to claim 6, wherein the distal tip structure of the catheter includes a dilator section having a recess configured to receive a proximal portion of an access section therein.

10. The method according to claim 9, further including coupling the proximal portion of the access section with the recess of the dilator section using adhesive, bonding, or welding.

* * * * *